United States Patent [19]

Rehn

[11] Patent Number: 5,479,814
[45] Date of Patent: Jan. 2, 1996

[54] METHOD AND APPARATUS FOR DETECTING MERCURY VAPOR CONTENT OF UNCONSOLIDATED POROUS MATERIALS

[76] Inventor: Patty Rehn, 19005 Pinehurst Rd., Bend, Oreg. 97701

[21] Appl. No.: 223,556

[22] Filed: Apr. 6, 1994

[51] Int. Cl.⁶ .............................. G01N 1/00; G01V 9/00
[52] U.S. Cl. .................. 73/19.01; 73/864,51; 422/88; 436/25; 436/26; 436/81
[58] Field of Search ................ 73/19.01, 19.07, 73/864.51, 863.21; 422/88; 436/26, 25, 28, 73, 81

[56] References Cited

U.S. PATENT DOCUMENTS

| | | | |
|---|---|---|---|
| 3,730,683 | 5/1973 | Milly | 436/81 X |
| 4,065,972 | 1/1978 | Holub et al. | 73/864.52 |
| 4,565,786 | 1/1986 | Dunkhase et al. | 436/26 |
| 4,573,354 | 3/1986 | Voorhees et al. | 436/25 X |
| 4,993,874 | 2/1991 | Klusman | 73/863.21 X |
| 5,235,863 | 8/1993 | Bailey et al. | 73/863.21 X |

Primary Examiner—Hezron E. Williams
Assistant Examiner—Michael J. Brock
Attorney, Agent, or Firm—Herbert C. Schulze

[57] ABSTRACT

A method and apparatus for determining mercury vapor content of a body of earth for the purpose of ascertaining the mercury vapor content and correlating to the expected degree of mineralized character of the body of earth which includes the use of a strip of silver placed within a pocket in the body of earth involved and then after an appropriate exposure time analyzing the silver to determine the mercury vapor content by reason of absorption of vapor therefrom by the silver and the subsequent driving off and measuring thereof.

2 Claims, 3 Drawing Sheets

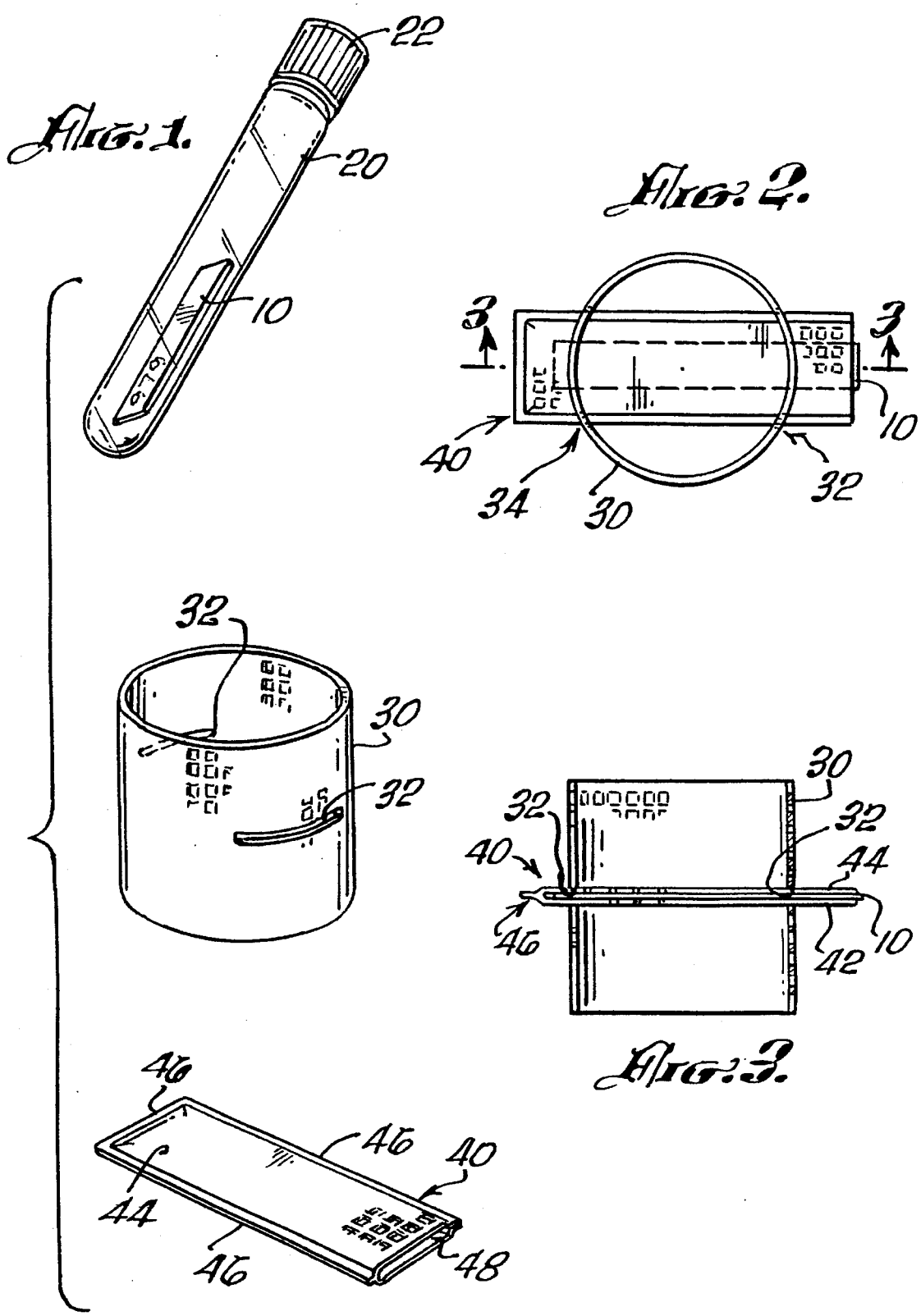

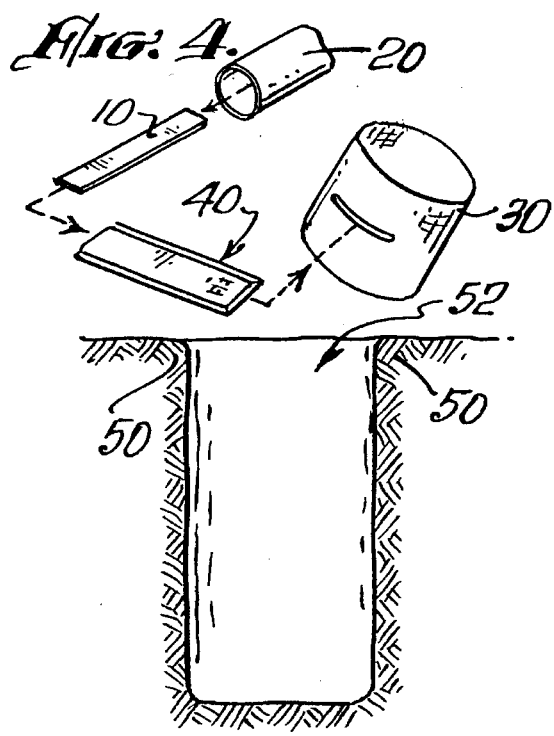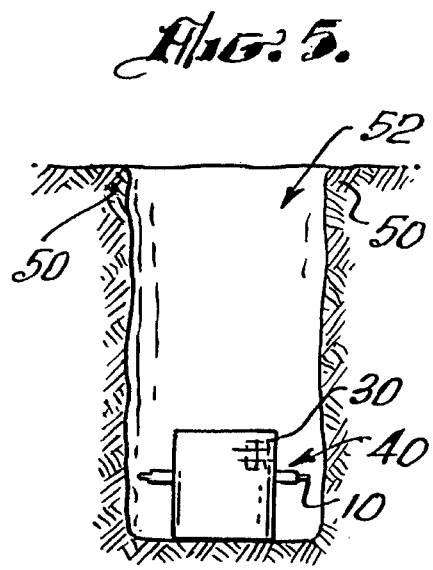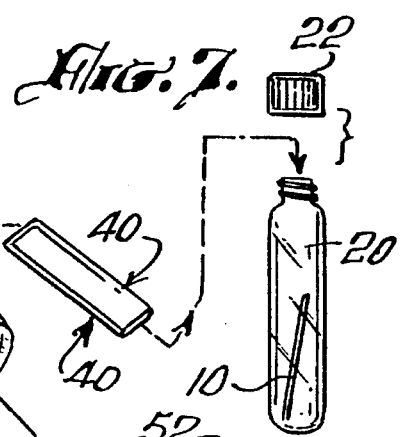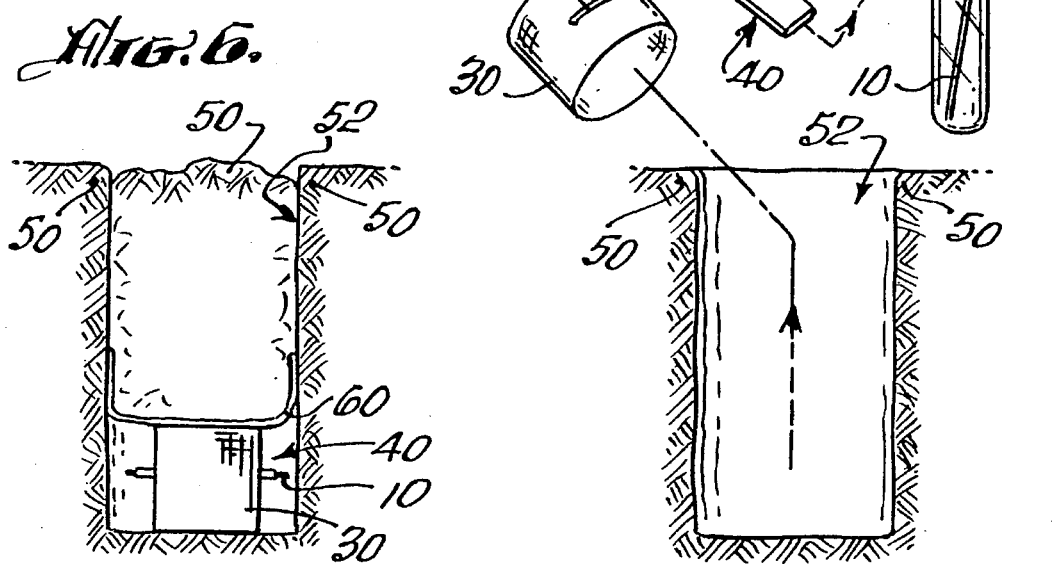

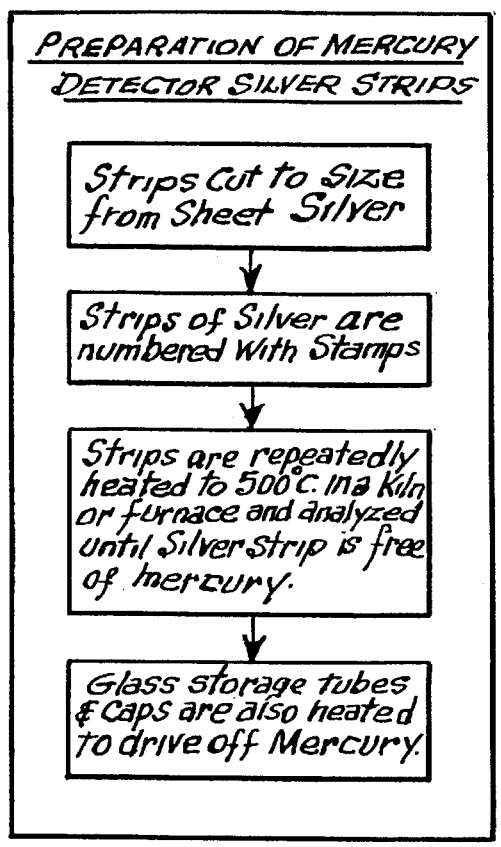

FIG. 9.

PREPARATION OF MERCURY DETECTOR SILVER STRIPS

- Strips Cut to Size from Sheet Silver
- Strips of Silver are numbered With Stamps
- Strips are repeatedly heated to 500°C in a Kiln or furnace and analyzed until Silver Strip is free of mercury.
- Glass storage tubes & Caps are also heated to drive off Mercury.

ANALYSIS OF MERCURY DETECTOR SILVER STRIPS

- Silver strips are recovered from the field burial and returned to the glass tubes and recapped.
- Glass tube and silver strip (w/o cap) are placed into a modified THERMOLYNE 21100 tube furnace and preheated for 30 seconds; to 500°C to evolve Hg gas from Ag.
- With the sample still in the furnace, a tygon tubing mounted pyrex probe is inserted into the tube and the analysis started.
- Hg analysis of the evolved gas is performed with an Arizona Instrument Gold Film Mercury Analyzer Model 511. Evolved gas is pumped (by analyzer) into the analyzer for 2 minutes, yielding a meter reading proportional to the nanograms of mercury absorbed to the Silver Strip.
- Standardization and the Construction of a Calibration Curve (meter response vs. nanograms Hg) is accomplished by injecting known amounts of mercury into the analyzer. Room air, free of mercury, is periodically analyzed to check for Instrument Contamination.
- Meter readings Converted to nanograms of Hg by means of Computer curve fit (Using Lotus 123).

METHOD AND APPARATUS FOR DETECTING MERCURY VAPOR CONTENT OF UNCONSOLIDATED POROUS MATERIALS

CROSS REFERENCE TO RELATED PATENT APPLICATIONS

There are no patent applications filed by me related to this patent application.

BACKGROUND OF THE INVENTION

I. Field of the Invention

This invention is in the general field of vapor analysis in unconsolidated porous materials;

The invention is more particularly related to vapor analysis in unconsolidated porous materials to determine the possible mineralized character of a body of earth by detecting mercury vapor content and for the purpose of detecting mercury vapor content for safety and environmental purposes; the invention is even more directly related to a method and apparatus for detecting mercury vapor content of unconsolidated porous materials by the use of silver strips to absorb mercury vapors to be analyzed later by removal of the absorbed mercury vapor from the silver in order to ascertain the amount of mercury which was in the unconsolidated porous material.

DESCRIPTION OF THE PRIOR ART

It has been known in the past to take specified quantities of earth material and to drive off any mercury vapor content in a laboratory and to measure it. Such procedures are not always satisfactory as the mercury vapor content in an isolated amount of material removed to a laboratory may be considerably different from the overall mercury vapor content of a large measurable body.

It is known that silver will absorb mercury vapor if exposed to it. It is further known such mercury vapor can amalgamate with silver. Mercury which has been amalgamated with silver can then be driven off under laboratory procedures such that the amount of mercury can be ascertained.

I know of no prior art wherein the principle of placing a piece of silver within the earth within a particular protective fashion has been considered for the purpose of analyzing the mercury vapor content of a large body of earth.

SUMMARY OF THE INVENTION

Mercury and hydrothermally deposited metals have been found to frequently exist in measurably related proportions within bodies of earth.

I have now discovered a method by which I can obtain an analysis which gives a reliable indication of the favorability of discovering hydrothermally deposited metals which may be present in any particular body of earth.

The method which I use comprises placing a measured amount of silver within the earth or ore body and leaving it for a pre-determined period of time during which it will absorb an amount of mercury which can be measured in a laboratory.

The same method and apparatus can be utilized to ascertain if dangerous levels of mercury are present in any particular place.

It is an object of this invention to provide a method and apparatus for determining the mercury vapor content of a body of earth;

Another object of this invention is to provide a reliable method of predicting the favorability of discovery hydrothermally deposited metals which may be in a particular body of earth through the analysis of the mercury vapor content;

Another object of this invention is to provide a method of ascertaining dangerous mercury levels within any particular body of earth.

The foregoing and other objects and advantageous of this invention will become apparent to those skilled in the art upon reading the description of a preferred embodiment, which follows, in conjunction with a review of the appended drawings.

BRIEF DESCRIPTION OF THE DRAWINGS

FIG. 1 is a perspective of three elements utilized in practicing the method of this invention, a silver strip within a sealed container, a support element, and the envelope to hold the silver strip within the support element;

FIG. 2 is a top elevation of the silver strip in its envelope and supported by the supporting element;

FIG. 3 is a section on 3—3 of FIG. 2;

FIG. 4 schematically illustrates the steps in placing the elements within a hole in the ground;

FIG. 5 illustrates what is used in conducting the test indicated within an open hole in the ground;

FIG. 6 relates the positioning of testing material with the hole being filled to the top of the test equipment by dirt;

FIG. 7 schematically illustrates the steps in preparing a silver strip which has been used in the test for transport to a laboratory for analysis;

FIG. 8 illustrates the silver strip in a sealed container ready to go to a laboratory;

FIG. 9 is a schematic worded description of the analysis method of this invention.

DESCRIPTION OF A PREFERRED EMBODIMENT

FIG. 1 shows a strip of silver 10 located within a glass tube 20 which has a threaded cap 22. The silver may be of any desired size and weight. Their forms such as a silver rod or the like could be utilized but I have found the silver strip to be preferable. The number is shown imprinted on the strip 10. This number is merely an identification number for control purposes of each individual strip which may be used in practicing this invention. The perforated cylinder 30 made of needlepoint canvas (known to those skilled in the art) has two slits 32 suitable to accommodate the envelope 44 as shown. There is no particular size requirement for any of these items. The envelope 40 is composed of a top 44, a bottom 42, sealed edges 46, and one open end 48 into which the silver strip can be inserted. The needlepoint canvas is very important, since it will not be contaminated and will not contaminate the silver. Another material with these qualities might be used.

FIG. 4 illustrates the silver strip 10 being removed from the tube 20 and placed into the envelope 40. The envelope 40 is inserted into the envelope holder 30 and then placed into the hole 52 in the earth or ore body 50. The holder, envelope, and silver strip are shown in place within the hole 52 in FIG. 5. The previous canvas or the like cover 60 is placed upon the holder 30 and dirt 50 is then refilled into the hole 52 supported by the cover 60. The silver strip is now exposed to gases emanating from the earth or ore body, but not exposed to the atmosphere.

After a pre-determined time the earth or ore filling the hole above the test strip is removed when the test strip is removed and placed in the vial 20 as shown in FIG. 7. The steps are the removal of the entire assembly from the hole, the removal of the silver strip from the envelope, and the placing of the silver strip within its vial. The vial is then sealed by the cap 22. The silver is then transported to a laboratory. FIG. 9 shows the actual steps.

It is to be particularly noted that when the silver strips are heated to determine the amount of mercury absorbed, the glass storage tube is also heated in order to be sure that none of the absorbed mercury somehow was left within the tube by accident.

For completeness of this specification, the steps and information indicated in FIG. 9 are repeated.

Strips of silver are cut to a desired size from a sheet of silver material. Each strip of silver is numbered, as indicated in FIG. 1 wherein the number 070 is indicated on that particular strip. The numbered strip is then identified by its actual weight and size. Prior to the final identification of each silver strip it is thoroughly heated to be sure that any and all mercury or other contaminants have been driven off.

The strips together with their storage tubes and caps are heated together. The silver strip, while it remains within the sealed tube, is not subjected to any mercury contamination.

After the exposure of the silver within the ground as previously described, the silver strip is once again returned to the glass tube and re-sealed.

The silver strip is then taken to a laboratory where it is placed into a modified thermolyne 211002 furnace or equivalent and preheated thirty seconds to 500 degrees centigrade to evolve mercury gas from the silver (the modification is merely the insertion within the furnace of a ceramic post or a glass tube support). The glass tube with the silver is heated without the cap. With the sample silver strip still in the furnace a tiglon tubing mounted pyrex probe is inserted into the tube and the analysis is commenced.

The mercury analysis of the evolved gas is by an Arizona Instrument gold film mercury analyzer model 511. The evolved gas is pumped into the analyzer for two minutes using a meter reading proportional to the nanograms of mercury absorbed by the silver strip.

Standardization and construction of a calibration curve is accomplished by injecting known amounts of mercury into the analyzer.

Ordinary room air, free of mercury, is periodically analyzed to re-check instruments for contamination.

Meter readings are converted to nanograms of mercury by a computer curve, for example this can be done by using Lotus 1-2-3, known to those skilled in the computer arts.

While the embodiments of this invention shown and described are fully capable of achieving the objects and advantages desired, it is to be understood that these embodiments have been shown for purposes of illustration and not for purposes of limitation.

I claim:

1. Apparatus for determining mercury vapor content of earth comprising a sleeve formed of needlepoint canvas; a silver strip within said sleeve; means to elevate said sleeve with said silver above a base upon which the means to elevate rests and a permeable covering over said sleeve and silver and means to elevate.

2. Apparatus for determining mercury vapor content comprising: a quantity of silver; a mercury permeable holder for said silver comprising a sleeve and a cylinder supporting said sleeve, both of which are formed of needlepoint canvas; and a permeable covering for said silver and holder.

\* \* \* \* \*